United States Patent [19]

Best

[11] 4,123,462
[45] Oct. 31, 1978

[54] AMINATION PROCESS USING NICKEL-RHENIUM CATALYSTS

[75] Inventor: Donald C. Best, Charleston, W. Va.

[73] Assignee: Union Carbide Corporation, New York, N.Y.

[21] Appl. No.: 647,065

[22] Filed: Jan. 7, 1976

[51] Int. Cl.$^2$ .................... C07C 85/00; C07C 85/02; C07C 85/06; C07C 85/08

[52] U.S. Cl. .................. 260/585 B; 252/454; 252/455 R; 252/457; 252/458; 252/459; 252/462; 252/463; 252/465; 252/466 R; 252/470; 252/471; 252/472; 252/473; 252/474; 260/583 P; 260/585 R; 260/585 A; 260/585 C; 260/585 D; 544/358; 544/402

[58] Field of Search ......... 260/585 B, 268 SY, 585 R, 260/566 R, 585 C; 252/455 R, 459, 466 J, 432

[56] References Cited

U.S. PATENT DOCUMENTS

| 3,022,349 | 2/1962 | Lemon et al. | 260/585 B |
| 3,152,185 | 10/1964 | Zvejnicks | 260/583 K |
| 3,223,735 | 12/1965 | Scholz | 260/585 R |
| 3,270,059 | 8/1966 | Winderl et al. | 260/583 |
| 3,387,032 | 6/1968 | Leonard | 260/585 B |
| 3,520,933 | 7/1970 | Adams et al. | 260/585 B |
| 3,666,412 | 5/1972 | Sowards | 252/432 X |
| 3,739,029 | 6/1973 | Magoon et al. | 260/585 A |
| 4,036,883 | 7/1977 | Voges et al. | 260/585 B |

FOREIGN PATENT DOCUMENTS 47-34181  11/1972  Japan ................. 260/585 B

Primary Examiner—Winston A. Douglas
Assistant Examiner—John J. Doll
Attorney, Agent, or Firm—Robert C. Brown

[57] ABSTRACT

The present invention concerns a new nickel-rhenium catalyst and method of preparing said catalyst. The invention also relates to the catalytic amination of lower aliphatic alkane derivatives such as alkanemono-ols, alkanediols and alcoholamines utilizing the new nickel-rhenium catalyst.

16 Claims, No Drawings

AMINATION PROCESS USING NICKEL-RHENIUM CATALYSTS

BACKGROUND OF THE INVENTION

A considerable number of methods for production of alkylamine products have been proposed and a number of them have been commercially utilized. The present invention particularly concerns the production of lower alkylamines by the catalytic amination of lower aliphatic alkane derivatives such as mono- and polyhydric alcohols, alcoholamines, and compounds from which these alcohols are derived, including epoxides, ketones and alkyleneimines.

The catalytic amination of alcohols is a process which has been long recognized in the prior art. It generally concerns the reaction of alcohol with ammonia in the presence of a hydrogenation catalyst and usually in the presence of hydrogen.

The most difficult problem in the manufacture of amines by this and other proposed processes is that the chemical synthesis reactions used also form substantial amounts of by-products, which are of considerably less value and as a result often render the synthesis inefficient and not commercially feasible.

The most desirable amine products generally are those products wherein an amine group replaces the non-amine functional group or groups in the alkyl starting material without any further modification of the starting material. Most heavier, more highly substituted amines and heterocyclic nitrogen compounds can be further synthesized from these preferred alkylamines. A synthesis of these heavier, substituted, and heterocyclic amines directly from the alkyl starting materials usually yields other unwanted by-products.

The amine products produced in accordance with the present invention have many uses. In addition to their use as intermediates for synthesizing other chemical materials, they are utilized, for example, in fungicides and insecticides.

For convenience in the description of the invention hereinbelow, the amination of ethylene glycol and monoethanol amine to ethylenediamine and other products will be most comprehensively discussed, although the present invention is not limited to these starting materials.

The amination of ethylene glycol may be illustrated by the following chemical formula with the primary products usually being monoethanolamine (MEA), ethylenediamine (EDA), and piperazine (also termed diethylenediamine, DEDA) and aminoethylethanolamine:

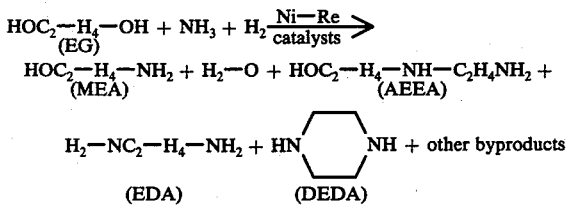

$HOC_2-H_4-OH + NH_3 + H_2 \xrightarrow[\text{catalysts}]{\text{Ni—Re}}$
(EG)
$HOC_2-H_4-NH_2 + H_2-O + HOC_2-H_4-NH-C_2H_4NH_2 +$
(MEA) (AEEA)

$H_2-NC_2-H_4-NH_2 + HN\diagup\diagdown NH$ + other byproducts
(EDA) (DEDA)

Numerous other chemical reactions are known for producing alkylamines. For example, in the synthesis of ethylenediamine, the following reactions have been proposed: the hydrolysis of ethylene urea; reductive amination of formaldehyde cyanohydrin; the reduction of cyanogen; the reduction of 1,2-dinitroethane; and the amination of chloroacetylchloride followed by reduction. None of these chemical processes appear to have been operated on a commercial scale because of the process requirements and costs of raw materials.

One of the most widely used commercial processes for producing ethylenediamine today involves a reaction of ethylenedichloride with aqueous ammonia. The ethylenedichloride is reacted with aqueous 30 to 40% ammonia to produce a dilute aqueous solution of amines. Sodium hydroxide is then added to neutralize the hydrochloric acid formed in the ammonia-ethylene dichloride reaction. This neutralization step forms additional water and gives rise to by-product sodium chloride. An illustration of the approximate distribution or profile of products produced by such a process is as follows:

| Products | Wt. % of Production |
|---|---|
| Ethylenediamine (EDA) | 41% |
| Diethylenetriamine (DETA) | 25% |
| Triethylenetetramine (TETA) | 10% |
| Tetraethylenepentamine (TEPA) | 8% |
| Pentaethylenehexamine (PEHA) | 13% |
| Polyamine Heavies (PAH) | 13% |
| Piperazine (DEDA) | 1.5% |
| Aminoethylpiperazine (AEP) | 1.5% |

About 2.5 lbs. of sodium chloride is produced per lb. of the amines produced.

Although the product distribution is commercially feasible, the presence of chlorine in the system, including in the corrosive form of hydrogen chloride, causes expensive maintenance costs. Moreover, recovery of the desired amine products from the salt-containing aqueous solutions is difficult and the disposal of the large quantities of salt is an ever increasing environmental problem. The cost of the starting materials also has been a discouraging factor.

A method which has recently emerged commercially is the reduction of amino acetonitrile to form ethylenediamine. Although this process, according to the literature can be operated to produce as much as 90% ethylenediamine in the amine yield, the expense of the starting materials in the process and other economic considerations do not make this process commercially attractive.

As indicated above, the catalytic amination of alkane derivatives including aliphatic alcohols and aminoalcohols has been the subject of much investigation and prior art literature. The applicant has now discovered a new catalyst which is both more active and more selective than previously known catalysts for carrying out amination processes. It should be noted that there are numerous materials which have the ability to catalyze such amination processes, but the mere ability to catalyze is far from sufficient to accord a catalyst one of commercial significance.

U.S. Pat. No. 2,861,995 describes a method of converting ethanolamine to various nitrogen-containing products by using a metal hydrogenation catalyst comprising one or more of nickel, cobalt, copper chromite, catalytic noble metal such as platinum and palladium, and Raney nickel and Raney cobalt. They may be supported on a carrier such as alumina.

U.S. Pat. No. 3,068,290 describes a process for converting ethanolamine to ethylenediamine by using a hydrogenation catalyst, such as described above, in a reaction which is in the liquid phase, under autogenous pressure. The patent also describes a preferred catalyst which is a combination of nickel and magnesium oxides (Ni-MgO), obtained by thermal decomposition of co-precipitated nickel and magnesium formates or oxalates.

U.S. Pat. No. 3,137,730 teaches the conversion of ethylene glycol by using a supported catalyst comprising nickel and copper. U.S. Pat. No. 3,270,059 teaches an amination process in the presence of a supported catalyst which is produced by sintering oxygen compounds of either nickel or cobalt at temperatures in excess of 700° C and reducing the sintered metal compound by treatment with hydrogen. U.S. Pat. No. 3,766,184 describes a catalyst containing iron with either nickel, cobalt or mixtures thereof. Ruthenium catalysts are also referred to in this and other patents as useful in amination processes.

None of the catalysts heretofore known have been commercially successful because of one or more inadequacies. Modern commercial catalytic processes require catalysts to be more than active, i.e., yield high conversions in the chemical reactions they catalyze. In the case of amination processes where numerous competing reactions occur yielding many by-products, it is important for the catalyst to have good selectivity or the ability to afford a high yield of useful product with a concomitant small yield of undesired product. The optimum reaction conditions including temperature, pressure and relative proportions of reactants, as well as reaction time, may be determined by the catalyst, and in so doing may affect the economics of the whole process. The cost of the catalyst, its method of preparation and its effective life as well as its physical properties may be determinative of a successful, viable process.

The applicant has now discovered a new catalyst containing nickel and rhenium, supported on a material selected from α-aluminas, silica, silica-aluminas, silica-titanias, and kieselguhrs, or diatomaceous earths which have improved properties over those catalysts heretofore known for catalyzing the amination of aliphatic lower alkyl derivatives.

SUMMARY OF THE INVENTION

This invention relates to a new catalyst comprising a mixture of nickel and rhenium impregnated on various support materials including α-alumina, silica, silica-alumina, kieselguhrs or diatomaceous earths and silica-titania which are active and selective in the conversion of various alkane derivatives to desirable amine products. It has been found that these nickel-rhenium catalysts not only exhibit excellent conversion activity but at the same time have superior selectivity in the production of greater amounts of desired amine products yet comparatively smaller quantities of less desired by-products. The nickel-rhenium catalyst of the present invention are hydrogenation catalysts and may be used in other processes in addition to amination processes.

The nickel-rhenium catalysts of this invention possess a wide spectrum in magnitude of catalytic activity; can be used in relatively small concentrations; permit the use of a better balance of reactants; and enable the use of resonable reaction conditions for carrying out the processes.

The applicant has further discovered that by controlling certain variables both in the preparation of the catalyst and in the catalytic amination process itself, the activity and selectivity of the amination reaction can be even further optimized and improved.

It has also been found that other metals may be present in the catalyst in admixture with the nickel and rhenium.

It has additionally been discovered that the nickel-rhenium catalyst of the present invention has surprising activity and selectivity in the amination of a wide range of alkane derivatives including, for example, epoxides, monohydric and polyhydric alcohols, ketones, alkaneimines and aminoalcohols.

DETAILED DESCRIPTION OF THE PREFERRED EMBODIMENTS

According to the present invention there are provided new catalysts having high activity and selectivity in amination processes, said catalysts comprising rhenium (atomic number 75) and nickel impregnated on a support material selected from α-alumina, silica, silica-aluminas, kieselguhrs or diatomaceous earths and silica-titania, wherein the mole ratio of the nickel to the rhenium is in the range of from 2:1 to about 30:1 and the total nickel and rhenium metal present is in the range of 3-30% by weight of the support.

Another feature of the present invention is a process for preparing said nickel-rhenium catalyst, said process comprising (i) impregnating a mixture of metals comprising rhenium and nickel on a support material selected from the group consisting of α-alumina, silica, silica-alumina, kieselguhrs or diatomaceous earths, and silica-titanias; and (ii) activating said catalyst by heating the catalyst in the presence of hydrogen at a temperature in the range of about 200°–600° C for a period of about 45 minutes to about 4 hours.

A further feature of the present invention is a method for producing lower aminoalkanes by the catalytic amination of lower aliphatic alkane derivatives including epoxides, alkanemono-ols, alkanediols, alkanolamines, ketones, iminoalkanes and iminoalkanols and mixtures thereof, said process comprising contacting said lower alkane derivatives with ammonia at a temperature of from 125° to 350° C and in the presence of hydrogen and the nickel-rhenium catalyst as described hereinabove.

The amination of alcohols involves a reaction between ammonia and alcohol in the presence of hydrogen gas. The amination process consists of a series of hydrogenation and dehydrogenation catalytic reactions. The mechanism of these various reactions have been extensively discussed in the prior art literature and are illustrated in the seven reaction formulas below:

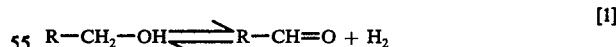

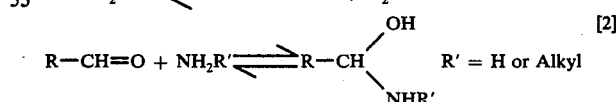

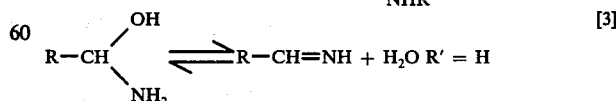

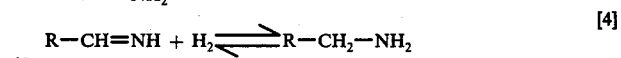

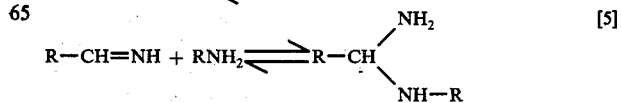

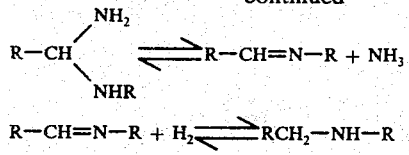

$$R-CH=N-R + H_2 \rightleftharpoons RCH_2-NH-R \quad [7]$$

The first step in the amination process is believed to be a reversible dehydrogenation of the alcohol to give an intermediate carbonyl [1]. The aldehyde is then converted to an aminoalcohol [2] by reaction with ammonia or an amine present in the reaction mixture. The aminoalcohol then loses water to form the imine [3]. The imine is then hydrogenated to the amine [4]. Where the intermediate aldehyde or the imine react with amines in the reaction mixture, substituted and heavier amines are formed. Formulas 5, 6, and 7 illustrate the possible products formed by a reaction of the intermediate imine with ammonia or amines present in the reaction mixture. The products most often present in the reaction mixture where ethylene glycol or monoethanolamine are the starting materials, include:

Ethylene Glycol (EG)
Monoethanolamine (MEA)
Ethylenediamine (EDA)
Piperazine (DEDA)
Diethylenetriamine (DETA)
Aminoethyl ethanolamine (AEEA)
Aminoethyl piperazine (AEP)

One of the major shortcomings in the previously known techniques in synthesizing the more desirable alkylamines and diamines is the simultaneous production of substantial amounts of less desirable by-products.

The production of excessive amounts of undesirable materials means an inefficient utilization of raw materials and additional problems incurred in separating the desired products from the reaction mixture and disposing of the waste products. A recent analysis of the current and forecasted demands of the pertinent nitrogen-containing products indicates that the greatest demand is for ethylenediamine. On the other hand, there is little if any demand for piperazine (DEDA) and only limited demand for derivatives of piperazine like aminoethyl piperazine (AEP). As a result, the selectivity of amination catalysts to produce a favorable distribution of products is illustrated herein by comparing the amount of ethylenediamine (EDA) produced by the process with the amount of piperazine (DEDA) produced for a given conversion.

There has therefore been great demand for a catalyst which has the ability to obtain high amination conversion rates yet maintain good selectivity in the products produced. The nickel-rhenium catalyst of the present invention has been sown to have these and other advantages in the amination of lower alkanes having one or more functional groups.

The nickel-rhenium catalysts of the present invention are solid catalysts wherein the nickel and rhenium metals are supported on certain materials many of which have been known for use as supporting materials for other catalysts.

The support materials which have been found to produce the most active and selective amination catalysts are those supports which are composed of silica, silica-alumina, α-alumina, silica-titania, and kieselguhrs or diatomaceous earths. Most of these support materials are well-known in the art and are commercially available.

Support materials are not equivalent in their ability to form active Ni-Re catalysts. For example, carbon supported Ni-Re catalysts using CXC carbon from National Carbon Company even with large surface areas, have not shown appreciable catalytic activity in amination reactions. Silica-magnesia supported Ni-Re catalysts have also not shown appreciable catalytic activity in amination processes.

Even the aforementioned support materials which have yielded active Ni-Re catalysts are not equivalent. Those supports which form more active catalysts yield optimum amination conversions at less severe reaction conditions, e.g., lower reaction temperatures. Therefore, although all supports tested within the group indicated above show some catalytic activity in the amination reaction, some supports within a general type have not been considered as having strong commercial promise because more extreme reaction conditions, such as higher reaction temperatures, must be used to obtain satisfactory conversions.

The actual effectiveness of a material as a support in a Ni-Re catalyst is generally not predictable in advance. However, among the general types of supports indicated above that have been found active, there appears to be some relationship between catalytic activity and the amount of surface area of the particular support materials.

One possible explanation for the surface area effect on catalyst activity is that a number of reactions in the amination process occur on the catalyst surface and are therefore effected by adsorption-desorption equilibria of the reaction materials. The activity of a nickel-rhenium catalyst would therefore be effected, within certain limits, by varying surface area of the supports and other surface properties including support shape, pore size, and pore volume. Generally, greater dispersion of the nickel and rhenium metals on higher surface area active supports produce more active Ni-Re catalysts.

Specific examples of some of the more active support materials for the Ni-Re catalyst of the present invention are listed in the table below:

TABLE 1

| Support | General Type | Surface Area m$^2$/gm |
|---|---|---|
| Girdler T869 | Silica-alumina | ~60 |
| Girdler T1571 | Silica-alumina | ~150 |
| Girdler T372 | α-alumina | ~40 |
| Girdler T373 | Silica-alumina | 2–3 |
| Girdler K306 | Silica-alumina | ~250 |
| Girdler T2085 | Silica-alumina | ~113 |
| Girdler K10 | Silica-alumina | ~268 |
| Girdler T2045 | Kieselguhr | |
| Norton LA 4102 | α-alumina | 1 |
| Johns-Manville Type III | Diatomaceous silica | 10–15 |
| Grace 980-13 | Silica alumina | ~375 |
| Grace 980-25 | Silica alumina | ~375 |
| Laboratory | Silica titania (SiO$_2$/TiO$_2$ Mole Ratio 9:1 to 1:9) | ~75–115 |

In the amination reactions of the present invention, Ni-Re catalysts comprising active supports having a surface area of 1 m$^2$/gm or greater are preferred.

The particular size and shape of the support material has not been found to have any appreciable effect on the catalytic properties of Ni-Re catalysts formed therefrom. The support materials which may be used in making the Ni-Re catalyst may be of any convenient shape or size. The shape of the support usually will depend upon the shape required in the particular apparatus used to perform the catalytic conversion reaction. Successful Ni-Re catalysts have been made on support materials in the form of powders, spherical pellets and extruded strips. Impregnated spherical pellets ranging in diameter from ⅛ inch to 3/16 inch have been used. Extruded strips of a cylindrical-type shape ranging from 1/32 inch to ½ inch in length are typical of those which can be used as successful supports for Ni-Re catalysts of the present invention.

The particular method of impregnating or coating the nickel and rhenium metal onto the support material has not been found to have a significant effect on the activity or selectivity of the final catalyst in amination processes. However, the amount of metal impregnated onto the support material and the nature of the support itself, as discussed above, does affect or vary the catalytic activity and/or selectivity.

One technique for impregnating the nickel and rhenium onto the support is to use a solution of salts of the metals as a vehicle.

Various organic and inorganic nickel and rhenium salts may be used in impregnation solutions. Examples of suitable nickel-containing salts are anhydrous and hydrated nickelous nitrate [hydrate: $Ni(NO_3)_2 \cdot 6H_2O$] and nickel acetonyl acetate [$Ni(C_5H_7O_2)_2$]. Suitable rhenium salts for use in the impregnating solution are ammonium perrhenate [$NH_4ReO_4$] and rhenium paradioxane [$Re_2O_7 \cdot 3(C_4H_8O_2)$]. In some cases, it is advantageous to heat the solvent liquid to bring the metal salts into solution.

The salt solution should be prepared by considering two factors. The first concerns the amount of total metal desired to be impregnated on a specific quantity of support. The second factor concerns the relative atom ratio of nickel to rhenium. Both factors have been found to affect the final properties of the catalyst.

The most active catalysts have been found to be those in which the Ni/Re atom ratio is between 2:1 and 30:1. In most cases, maximum activity occurs with a Ni/Re atom ratio between 5:1 and 20:1. Example 3 below demonstrates the effect varying Ni/Re atom ratio has on activity of the catalyst. In preparing the catalyst, the Ni/Re atom ratio is obtained by predetermining the corresponding relative proportions of the metal salts to be present in the impregnation solution.

The total metal to be impregnated onto the support also has an effect on the activity of the catalyst. Example 4 demonstrates that varying the metal loading has a different effect on a silica (Girdler T1571) and a silica-alumina (Girdler T869) supported catalyst. Example 4 indicates that the silica supported catalyst having a high surface area had greater activity with greater amounts of metal present. The silica-alumina supported catalyst, with a lower surface area than the silica support, had greater activity with 12.5% metal on the support as compared with 30% metal.

Ni-Re catalysts in accordance with the present invention contain a total nickel plus rhenium metal content in the range 3–30% by weight of the support material. Most Ni-Re catalyst exhibit maximum activity with Ni-Re contents in the range 5–15% by weight of the support.

Where relatively large amounts of metal are to be impregnated on supports with relatively low surface areas or possibly high densities, a single impregnation step may not be sufficient. Although an impregnation solution may be prepared with the minimum amount of solvent required to dissolve the metal salts, the total amount of the impregnation solution may be greater than that which the support material can absorb, or beyond the maximum absorption amount.

In such case, a portion of the impregnation solution less than the maximum absorption amount is used to initially contact the support material. After contacting, the support material is dried and then contacted with an additional amount of the impregnation solution. The sequential steps of contacting with solution and drying are continued until all of the impregnation solution is used. A typical drying step can comprise heating the impregnated support to a temperature of 120° C for several hours. Evacuation drying may also be used, where the support is cooled under reduced pressure.

It is also advantageous to dry the support material prior to impregnation in order to insure that the support will take up as much of the solution as possible. This pre-drying step also enables the metal to permeate more deeply into the support during impregnation. The penetration of the metal into the support may be further increased by techniques known to those skilled in the art such as by increasing the time the support is in contact with the solution.

Other impregnation techniques are well known in the art and may be utilized in the present invention. Another technique which can be used is often characterized as a "sugar coating" technique where the metal is predominantly present on the outer surface of the support material.

This sugar coating technique differs from the impregnation process described above by the addition of a precipitant at the time the impregnating salt solution is in contact with the support material. The precipitant converts the metal salt solution into a slurry. This impregnating vehicle reduces the penetration of the salts beyond the surface of the support material. The slurry in contact with the support material is then evaporated to dryness leaving the metal adhering predominantly to the support surface.

After the support material is impregnated with the desired amount of nickel and rhenium metal, it is completely dried and then activated by a reduction step.

The drying step to be used is any technique which sufficiently evaporates the volatile constituents of the impregnating solution. The drying step may comprise heating the catalyst to a temperature of about 120° C. The drying may be done under an inert atmosphere, such as nitrogen, and the catalyst may be cooled under reduced pressure.

The catalyst is then activated by a suitable step wherein the impregnated metal is converted into a catalytically active form. This activation may include alloy formation, proper phase orientation of the metals and/or an adjustment in the oxidation level of the metals. An activation step may include a typical reduction process.

In the preferred activation step the atmosphere in contact with the catalyst is hydrogen which is fed over the catalyst at an elevated temperature in the order of 200° to 600° C for periods of from about 45 minutes to about 4 hours. The specific conditions for reduction are dependent upon the particular catalyst composition being activated.

Prior to the activation step, the catalyst may be optionally calcined. In a preferred calcining step, the catalyst is heated to temperatures in the range of about 300° to 500° C for 45 minutes to about 3 hours or more. It is preferred that the calcining be carried out in air. The drying step referred to above may be replaced by the calcining step or activating step.

The nickel-rhenium catalysts of the present invention include catalysts which contain various other metals in admixture with the nickel and rhenium which do not detrimentally affect the catalytic properties of catalysts containing nickel and rhenium as the only impregnated metals. These additional metals, in certain amination processes, may actually improve selectivity and activity of the basic Ni-Re catalyst. Certain of these metals may extend the activity life and other physical properties of the Ni-Re catalyst. Examples of catalysts containing additional metal components include Ni-Re-La, Ni-Re-Ca, Ni-Re-Mg, Ni-Re-Sr, Ni-Re-Li, Ni-Re-K, Ni-Re-Ba, Ni-Re-Ce, Ni-Re-W, Ni-Re-Fe, Ni-Re-Ru, Ni-Re-Cu, Ni-Re-Ag, Ni-Re-Zn, Ni-Re-Co, Ni-Re-U, Ni-Re-Ti and Ni-Re-Mn. In order to prepare such catalysts, salts of these additional metals are added in suitable amounts to the impregnation solution containing the nickel and rhenium salts.

An indicated above, the amination of alkane derivatives is a process which has been extensively investigated and is well documented in the prior art. The reaction conditions for the process to occur are generally known but are particularly dependent upon the activity of the amination catalyst present. When amination processes are catalyzed by the nickel-rhenium catalyst of the present invention, the conversion and activity of the reaction are significantly and surprisingly improved, and the reaction conditions required are generally less severe.

The alkane derivatives which may be aminated in accordance with the present invention include lower aliphatic alkane derivatives having one or more functional groups. Preferred lower aliphatic alkane derivatives include those containing one to six carbons. The functional groups present may be on the primary, secondary or tertiary carbon atoms. At least one of the functional groups present should be capable of being replaced by an amine group in the catalytic amination process of the present invention. The preferred functional groups include hydroxy, amino, imino groups and combinations of said groups. Illustrative examples of preferred alkane derivative starting materials include ethanol, ethylene-glycol (ethanediol), monoethanolamine, ethyleneimine, isopropanol, propanolamines, propanediols, acetone, butanols, butanediols, aminobutanols, pentanols, pentanediols, aminopentanols, hexanols, hexanediols and aminohexanols. The starting materials contemplated herein also include compounds from which the aforementioned may be derived. Preferably, at least one of the functional groups in the starting material is a hydroxy group. Other functional groups which are not replaceable during amination may be present in the alkane starting material in combination or in addition to the replaceable functional groups.

The particular alkane derivative starting materials to be used, of course, depends upon the particular amine product desired to be produced. Generally, the desired aminated product differs from the alkane starting material by the amine group which replaces the non-amine functional group or groups present in the starting material. For example, in the production of ethylene diamine, starting materials include ethylene glycol and monoethanol amine.

In the amination process of the present invention, the alkane derivative starting material is reacted at an elevated temperature with ammonia in the presence of hydrogen and the nickel-rhenium catalyst. The temperature for the reaction depends upon the particular starting material, ratios of reactants, and most importantly, the activity of the catalyst used. Generally, in processes of the present invention, temperatures within the range of 125° C to 350° C are suitable while a preferred range is 150°-225° C.

A relatively high pressure for the reaction is also preferred. Normally, the increased pressure is obtained by the desired amount of ammonia and hydrogen already present in the reaction vessel, which is then heated to the reaction temperature. The pressure at the time of reaction should normally be within the range from about 500 to about 5,000 psig and preferably from 800 to about 4,500 psig. The reaction may occur in a single phase or in two phases where some of the ammonia and some of the alkane starting material are present in the liquid phase and some in the gaseous phase.

The ammonia employed in the reaction may be anhydrous or may contain small amounts of water. Any water introduced into the reaction mixture with the ammonia should be considered when conversion of the reaction is evaluated by the presence of water in the final mixture.

Normally, the process is run in an excess of ammonia to ensure reactions with ammonia and not an amine present in the reaction mixture. This is one means of improving the yield of the desired aliphatic alkylamine product. In some catalytic systems a large excess of ammonia must be present. One advantage of the present invention is that because of the exceptional selectivity of the nickel-rhenium catalyst of the present invention, only a relatively small excess of ammonia is required.

It has been found that increasing the mole ratio of ammonia to the alkane derivative reactant decreases the activity or conversion rate of the reaction in some types of reactors. This occurrence may be due to the fact that excessive amounts of ammonia will reduce the amount of surface of the catalyst available for access by the alkane derivative reactant.

In the amination processes of the present invention, the ammonia should be present in an amount at least equivalent to the stochiometric amount required by the alkane derivative reactant. The ammonia should preferably be present in an amount between 2 times and 30 times the stochiometric amount required.

In the production of ethylene diamine from ethyleneglycol, monethanolamine or mixtures thereof, ammonia is preferably present in an amount to give a mole ratio of total EG and MEA to ammonia in the range of 1:4 to 1:20.

The amount of hydrogen gas present in the amination process of the present invention is not critical. Usually, hydrogen is added in an amount sufficient to maintain the catalyst in an active state. A preferred amination process is carried out where the hydrogen is present in an amount wherein the hydrogen to ammonia mole ratio is greater than 1 and preferably less than the ratio 1000:1.

Where selectivity is of primary concern in the amination process, it is preferred not to run the process to a high conversion. It has been found that selectivity to the preferred aminoalkanes decreases as conversion increases.

One possible explanation for why selectivity decreases as conversion increases is that the heavier and more substituted nitrogen products are produced as a result of a chain of consecutive reactions. For example, it has been suggested that the piperazine by-product formed in the amination of monoethanol amine is produced by either route 1, 2 or 3 shown below:
(1) MEA → EDA → AEEA → piperazine (DEDA)
(2) MEA → EDA → piperazine (DEDA)
(3) 2MEA → AEEA → piperazine (DEDA)

The amination process of the present invention may be carried out in any conventional equipment having heating means. The process may be carried out as a continuous process of by batch. In continuous equipment no agitating means is required as the nature of the continuous process causes the reactants to continually flow in intimate contact with the catalyst material. Where high pressures are desired for the amination process, the equipment should have high pressure capability.

The amount of Ni-Re catalyst present in an amination process depends on many variables including the reactants, the relative proportions of the reactants, reaction conditions, and the degree of conversion and selectivity desired. Moreover, the amount of catalyst will depend also on the nature of the catalyst itself, e.g., its metal loading and activity and age. In sum, the catalyst should be present in the amination reaction in sufficient catalytic amount to enable the desired reaction to occur.

In the examples below, some of the materials used were obtained from the following sources:

Girdler supports were obtained from the Girdler Division of Chemetron Corporation, P.O. Box 337, Louisville, Ky.

Norton supports were obtained from the Norton Company, Akron, Ohio.

The Johns Manville supports were obtained from Johns Manville Products Corporation, 8741 Americana Blvd., Indianapolis, Ind. 86268.

Ammonium perrhenate (NH$_4$ReO$_4$) was obtained from Cleveland Refractory Metals, 28850 Aurora Road, Solon, Ohio 44139.

Nickelous nitrate [Ni(NO$_3$)$_2$.6H$_2$O] was J. T. Baker analytical reagent grade.

Other chemicals referred to in the examples are reagent grade and commercially available from numerous sources.

EXAMPLE 1

Analytical Method for Determining the Selectivity and Activity of an Amination Catalyst In order to develop catalyst activity data, analytical methods to permit the determination of the degree of reactant conversion and the product distribution are required. The degree of conversion, X, is defined by equation (1); and $$X_a = 1 - \frac{n_t}{n_o} = \frac{\text{moles MEA reacted}}{\text{moles MEA charged}} \quad (1)$$

where:
$n_t$ = moles present at time $t$
$n_o$ = moles present initially to determine $X_a$ at various reaction times, knowledge of the reactant-alcohol concentration-time profile is required.

The activities of the various catalysts tested have been ranked by determining the amount of water produced under standard reaction conditions. Each mole of MEA or EG converted produces a mole (or two moles in the case of EG) of water and the $$NH_3 + H_2NCH_2CH_2OH \rightarrow H_2NC_2H_4NH_2 + H_2O$$

$$2NH_3 + HOC_2H_4OH \rightarrow H_2NC_2H_4NH_2 + 2H_2O$$

catalyst producing the most water is the most active. The water produced is easily determined by Karl Fischer titration of the (ammonia free) reaction mixtures.

The selectivity of the catalyst is determined by analyzing the reaction product mixture and comparing the amount present of various reaction products. In the case of amination of ethylene glycol and monoethanolamine to produce ethylene diamine selectivity is determined by comparing the amount of ethylenediamine (EDA) with the amount of piperazine produced in a given conversion. The analysis of the reaction product mixture is generally done by gas chromatographic separation. Examples of columns which have been used in the gas chromatographic analysis of such reaction mixtures include TERGITOL NP-27 on CHROMOSORB T and TERGITOL E-68 on CHROMOSORB Z. A particularly preferred column comprises Carbowax 30M on Chromosorb 750 having a particle size of 40-60 mesh and wherein the column is 8 feet long having an inner diameter of ⅛ inch.

EXAMPLE 2

Comparison of Different Metals in Catalysts

This example concerns an evaluation of the activity and selectivity of various catalysts identified in Table No. 2. All of the catalysts used in this example were prepared by the same general technique.

Preparation of Impregnating Solutions

Stock solutions containing Ni, Cu, Pd, and Re were prepared by dissolving a known quantity of an appropriate metal salt in water. The metal salts, amounts used, and the final metal concentration are tabulated below.

| No. of Solution | Metal Salt | Mole Wt. | Gms. Salt | Gms. H$_2$O | Gms. Metal/ml soln |
|---|---|---|---|---|---|
| 1 | Ni(NO$_3$)$_2$ . 6H$_2$O | 290.8 | 66 | 300 | .05 |
| 2 | Pd Cl$_2$ | 177.3 | 6.6 | 380 + 70ml conc. HCl | .009 |
| 3 | Cu(NO$_3$)$_2$ . 3H$_2$O | 241.6 | 7.6 | 200 | .01 |
| 4 | NH$_4$ReO$_4$ | 268.2 | 8 | 100 | .056 |

Preparation of Catalysts

Nickel on Norton α-alumina LA-4102.

The support (19 grams) was placed in a 250 ml. round bottom flask, water (25 mls) and ethanol (25 mls) were added. After swirling, 20 mls. of solution No. 1 was added. A solution containing ammonium carbonate (3 gm) in 25 mls. of water was added dropwise to the metal-support slurry. The slurry was evaporated to dryness on a vacuum rotary evaporator. The coated catalyst was transferred to a porcelain evaporating dish, and dried at 120° C for 2 hours. The catalyst was then roasted at 300° C for 2 hours in a muffle furnace, cooled to room temperature, transferred to a quartz tube and placed in a tube furnace. The tube furnace was heated to 300° C, and the catalyst was reduced in a stream of hydrogen gas for 2 hours, 40 minutes. The quartz tube was purged with $N_2$ gas while cooling to room temperature, and the catalyst was stored under $N_2$ until tested.

Nickel on CXC Carbon, Nickel - JM - 408*, and Nickel-Girdler Silica, T869

* Johns Manville, Diatomaceous silica

These catalysts were prepared using the same procedure described for the preparation of the Ni -α- alumina catalyt. The carbon used was National Carbon Company's CXC 6/8 mesh.

Nickel-Copper Catalysts

These catalysts were prepared using essentially the same procedure as described above for the Ni -α- alumina catalyst. The amount of support used was increased to 38 grams, and a 500 ml. round bottom was used. After slurrying the support with a solution containing 50 mls. $H_2O$ and 40 mls. ethanol, 36 mls. of solution No. 1 followed by 20 mls. of solution No. 3 were added. This gives a Ni/Cu atom ratio of approximately 8.7/1. A solution containing 6 gm. of ammonium carbonate in 50 mls. of water was then added, and the resulting slurry was evaporated to dryness using a vacuum rotary evaporator. The drying, roasting, and reduction steps were conducted as described previously. The catalysts were stored under $N_2$ prior to testing. The Ni-Cu catalysts on CXC carbon was pyrophoric.

Ni-Pd Catalysts

These catalysts were prepared using a slight modification of the previous procedure. The support (38 gm.) was placed in a 500 ml. round bottom flask and 40 mls. Ethanol (200 proof) was added, followed by 32 mls. of solution No. 1 and 43 mls. of solution No. 2. This gives a slurry containing a Ni/Pd atom ratio of approximately 7/1. Powdered ammonium carbonate was then added portion wise until the PH of the slurry increased to approximately 8 (Hydrion paper). The slurry was then evaporated to near dryness using a vacuum rotary evaporator. The mass was reslurried in 50 mls. of fresh absolute ethanol and evaporated to dryness. The drying, roasting, and reduction steps were conducted as described above.

Ni-Re Catalysts

These catalysts were prepared using the procedure described for preparation of the Ni-Pd catalysts. Again, 38 grams of support was used, and after slurrying the supports in 50 mls. ethanol, 32 mls. of solution No. 1 followed by 7.2 mls. of solution No. 4 were added. This gives a Ni/Re atom ratio of approximately 11.3/1. The evaporation, drying, roasting and reduction steps were as described for the Ni catalysts. Two of the reduced Ni-Re catalysts were pyrophoric, Ni-Re on CXC Carbon and Ni-Re on JM-408 (diatomaceous silica).

The metal loading in each case was a maximum of 5 percent by weight of the support, assuming that 100 percent of the available metal was picked up by the support.

The catalysts were tested in a 0.5 liter rocker autoclave. In each case, the catalyst (5 gm.) slurried in MEA (25.5 gm., 0.42 moles), and water (5 gm., if any), was charged to the autoclave. The autoclave was pressurized with hydrogen to the required pressure (50 or 200 PSIG), and finally liquid ammonia (71 gm., 4.17 mole) was pressured into the autoclave via a hoke cylinder. The reaction mixture was heated to the required temperature (175 or 225) and held at reaction temperature for six hours.

The results of the 16 tests are reported in Table 2. The analyses of the product was done by the techniques described in Example 1. The most active catalysts tested was a Nickel-Rhenium based catalyst on α -alumina (run No. 13) which also exhibited a high degree of selectivity (EDA/DEDA). The Ni-Re catalysts on diatomaceous silica (JM-408) and silica (Runs 15 and 16) showed excellent selectivity but low conversion activity at the reaction conditions tested. The Ni-Re catalyst on the carbon support (Run 14) did not show any catalytic activity in the amination process.

TABLE 2
CONVERSION OF MONOETHANOLAMINE TO ETHYLENEDIAMINE

| Run No. | CATALYST | Run Temp. | $H_2$ PSIG | Ml $H_2O$ Charged | %$H_2O$ in Prod. | Approx. %MEA Converted | Products | EDA/DEDA |
|---|---|---|---|---|---|---|---|---|
| 1 | Ni on α-alumina | 175 | 50 | nil | 1.6 | 5 | EDA | ∞ |
| 2 | Ni on CXC Carbon | 175 | 200 | 5 | 1.9 | 6 | No Products Obsd. | — |
| 3 | Ni on JM-408** | 225 | 200 | nil | 6.4 | 22 | EDA, DEDA | 12.6 |
| 4 | Ni on Girdler Silica* | 225 | 50 | 5 | 4.2 | 14 | EDA, DEDA | 5.5 |
| 5 | Ni—Cu on α-alumina | 175 | 50 | nil | 0.9 | 3 | EDA | ∞ |
| 6 | Ni—Cu on CXC Carbon | 175 | 200 | 5 | 3.6 | 12 | No Products Obsd. | — |
| 7 | Ni—Cu on JM-408** | 225 | 200 | nil | 4.0 | 13 | EDA, DEDA | 9.9 |
| 8 | Ni—Cu on Girlder Silica* | 225 | 50 | 5 | 7.7 | 26 | EDA, DEDA | 1.0 |
| 9 | Ni—Pd on α-alumina | 225 | 200 | 5 | 4.4 | 15 | EDA, DEDA | 1.3 |
| 10 | Ni—Pd on CXC Carbon | 225 | 50 | nil | 4.7 | 16 | Trace EDA and anks | — |
| 11 | Ni—Pd on JM-408** | 175 | 50 | 5 | 1.7 | 6 | No Products Obsd. | — |
| 12 | Ni—Pd on Girdler Silica* | 175 | 200 | nil | 4.3 | 15 | EDA | ∞ |
| 13 | Ni—Re on α-alumina | 225 | 200 | 5 | 14.0 | 48 | EDA, DEDA | 4.75 |
| 14 | Ni—Re on CXC | 225 | 50 | nil | 3.4 | 12 | No Products Obsd. | — |
| 15 | Ni—Re on JM-408** | 175 | 50 | 5 | 0.6 | 2 | EDA | ∞ |
| 16 | Ni—Re on Girdler Silica* | 175 | 200 | nil | 2.6 | 9 | EDA | ∞ |

**Diatomaceous silica
*T869

EXAMPLE 3

Ni/Re Atom Ratio

For this example ten nickel-rhenium catalysts have been prepared on two support materials including Girdler supports T372 and T869.

All of these catalysts were prepared by the same general procedure. A solution containing $Ni(NO_3)_2$.

6H$_2$O and NH$_4$ReO$_4$ dissolved in 12 mls of distilled water was prepared.

The impregnation procedure involved adding the nickel-rhenium solution to 19 grams of dried, evacuated support material via a syringe. The impregnated support was dried in an oven at 120° C for several hours, and then placed in a muffle oven at a specified temperature (calcining temperature) for 3 hrs. to calcine the catalyst. After calcining, the catalyst was placed in a quartz tube and purged with a continuous nitrogen flow (10–20 cc/min.) while being heated to a record specified temperature. Upon reaching this temperature (reduction temperature) the flow of nitrogen was interrupted and hydrogen was fed at 10–20 cc/min through the tube for 3 hrs. to reduce the metal oxides and activate the catalyst. After this activation, the flow of hydrogen was interrupted and nitrogen was fed through the quartz tube and the catalyst was permitted to cool to room temperature (25° C). The activated catalyst was stored under nitrogen until used.

The above procedure is a general one and was used to prepare the ten nickel-rhenium catalysts.

These catalysts differed by the Ni/Re ratio, the calcining temperature, the reduction temperature, and the support used as shown in the Table 3. The amounts of Ni(NO$_3$)$_2$. 6H$_2$O and NH$_4$ReO$_4$ used to prepare the above catalysts were varied to give in each case a catalyst containing the desired Ni/Re atom ratio. All of the catalysts were prepared to contain 5 wt. % total metal (Ni + Re) on the support.

The above catalysts were tested for activity to convert monoethanolamine to ethylenediamine using a 0.5 liter Parr rocker autoclave constructed of stainless steel. The test procedure involved charging 5 grams of the appropriate catalyst, 26 gm (0.5 mole) of monoethanolamine, and 200 PSIG of hydrogen to the autoclave. Next, 72 grams of anhydrous ammonia was pressured into the autoclave, and the autoclave was heated to 200° C. The reaction temperature was maintained at 200° C for 1 hour and then the autoclave was allowed to cool to room temperature (~23° C). The excess ammonia was slowly vented from the autoclave, and the products were recovered essentially ammonia-free.

The crude, ammonia-free products were first analyzed for water content using the Karl Fisher titration method to determine the extent of monoethanolamine reacted.

TABLE 3

| Catalyst No. | Ratio Ni/Re | Calcining Temp. °C | Temp. °C Reduction | Girdler Support Used | % H$_2$O | EDA DEDA |
|---|---|---|---|---|---|---|
| 1 | 15/1 | 300 | 300 | T869 | 13.5 | Not run |
| 2 | 30/1 | 300 | 600 | T869 | 5.0 | 5.4 |
| 3 | 15/1 | 300 | 600 | T372 | 4.2 | EDA only |
| 4 | 30/1 | 300 | 300 | T372 | 5.7 | 24 |
| 5 | 15/1 | 600 | 600 | T372 | 3.9 | EDA only |
| 6 | 30/1 | 600 | 300 | T372 | 3.3 | Not run |
| 7 | 15/1 | 600 | 300 | T869 | 10.3 | 7.7 |
| 8 | 30/1 | 600 | 600 | T869 | 5.3 | Not run |
| 9 | 10/1 | 300 | 300 | T869 | 16.7 | 3.2 |
| 10 | 10/1 | 300 | 300 | T372 | 7.4 | Not run |

The data analysis of the products, namely the water content and product ratio of EDA to DEDA also appears in Table No. 3. The results indicate a clear dependence of catalyst activity on Ni/Re atom ratio. The data shows that the T869 supported catalysts with a 10/1 and 15/1 Ni/Re atom ratio are more active than those with a 30/1 Ni/Re atom ratio. Also, the T869 supported catalysts are more active than the T372 supported catalysts.

EXAMPLE 4

Varying The Ni-Re Loading

This example illustrates the effect on activity and selectivity of varying the total weight % of nickel+λ rhenium metal impregnated on the catalyst support.

Four catalysts were prepared having different amounts of total nickel and rhenium metal on Girdler T869 and T1571 supports.

12.5% Ni-Re on Girdler T1571

A solution containing 18.8 gms. of Ni(NO$_3$)$_2$. 6H$_2$O and 1.73 gms. NH$_4$ReO$_4$ dissolved in 52 mls. of water was prepared. 35 gms. of T1571 support was dried in an oven at 120° C and evacuated. 26 mls. of the above Ni-Re solution was slurried with the dried, evacuated support. The impregnated support was then dried, evacuated, and impregnated with a second 26 ml portion of the Ni-Re solution. The support was again dried, calcined, and reduced at 300° C for 3 hours in a stream of hydrogen.

30% Ni-Re on T1571 Support

A solution containing 45.12 gm Ni(NO$_3$)$_2$. 6H$_2$O and 4.12 gm of NH$_4$ReO$_4$ dissolved in 62 mls of water was prepared and used to impregnate 28 grams of Girdler T1571 support. The impregnation procedure was similar to that described for the 12.5% Ni-Re catalyst except that 21 mls of the above Ni-Re solution was used per impregnation. A total of 3 impregnations were required to absorb all of the Ni-Re on the support. The impregnated support was calcined at 300° C for 3 hours, and then reduced for 3 hours at 300° C in hydrogen.

30% Ni-Re on T869 Support

A solution prepared by dissolving 45.12 gm Ni(NO$_3$)$_2$. 6H$_2$O and 4.12 gm NH$_4$ReOH in 59 mls of water was used to impregnate 28 gms of Girdler T869 support. The impregnation required 4 coatings with 15 mls of the Ni-Re solution per coating. The impregnated support was calcined at 300° C for 3 hours and then reduced in a stream of hydrogen for 3 hours at 300° C.

12.5% Ni-Re on T869 Support

A solution of 18.8 gm of Ni(NO$_3$)$_2$. 6H$_2$O and 1.73 gm of NH$_4$ReO$_4$ in 37 mls of water was prepared, and used to impregnate 35 gms. of Girdler T869 support. The impregnation required 2 coatings with 18.5 mls of the Ni-Re solution per coating. The impregnated catalyst was calcined for 3 hours at 300° C and reduced for 3 hours at 300° C.

The above four catalysts were tested for activity and selectivity in the conversion of ethylene glycol to ethylenediamine, monoethanolamine, and piperazine in a 0.1 Parr rocker autoclave constructed of stainless steel. The procedures used to charge the autoclave, and analyze the products were identical to those described in Example 2 above. The specific reaction conditions are set forth in the table below. The reaction time for each experiment was 45 minutes where the reaction times were measured after the reaction mixture reached the desired reaction temperature.

TABLE 4

| Exp. No. | Girdler Catalyst Support Used | Weight % Total Metal On the Support | Feed Mole Ratio NH$_3$/EG | Reaction Temp. °C | Weight % H$_2$O in Product | Product Ratio EDA/DEA |
|---|---|---|---|---|---|---|
| 1 | T1571 | 12.5 | 13/1 | 200 | 10.3 | 3.0 |
| 2 | T869 | 12.5 | 13/1 | 225 | 30.8 | 0.6 |
| 3 | T1571 | 30.0 | 13/1 | 225 | 32.2 | 0.7 |
| 4 | T869 | 30.0 | 13/1 | 200 | 10.9 | 4.3 |
| 5 | T1571 | 12.5 | 20/1 | 225 | 10.3 | 2.4 |
| 6 | T869 | 12.5 | 20/1 | 200 | 7.3 | 13.0 |
| 7 | T1571 | 30.0 | 20/1 | 200 | 9.2 | 10.6 |
| 8 | T869 | 30.0 | 20/1 | 225 | 15.7 | 4.4 |

The respective feeds of reactants in each of the experimental runs are as follows:

| Exp. Nos. | Gms NH$_3$ | Gms. EG | Gms. Catalyst | Initial H$_2$ Press |
|---|---|---|---|---|
| 1,2,3,4 | 68.0 | 19.0 | 5.0 | 200 PSIG |
| 5,6,7,8 | 104.0 | 19.0 | 5.0 | 200 PSIG |

Analysis of the data from the eight experimental runs of Table 4 show that the 12.5% metal catalyst supported on T869 is more active than the 30% metal catalyst supported on T869. Conversely the 30% metal catalyst supported on T1571 is more active than the 12.5% metal catalyst supported on T1571. The data confirms that the degree of ethyleneglycol conversion can be increased either by increasing the reaction temperature from 200° C to 225° C, or by decreasing the NH$_3$/EG feed mole ratio from 20/1 to 13/1.

EXAMPLE 5

Amination Reaction Conditions

This example demonstrates that Ni-Re based catalysts are active for converting ethylene glycol to ethylenediamine, monoethanolamine, and piperazine. Also shown is the effect of the various reaction variables on the conversion of ethylene glycol.

A. Preparation of Catalysts

Two batches of nickel-rhenium based catalysts supported on Girdler supports T869 and T1571 were prepared. Each of the catalyst supports was impregnated with 5 weight % total metal (as Ni° + Re°) having a Ni/Re atom ratio of 10/1. The supports were impregnated as described below.

Preparation of 5% Ni-Re on Girdler T869

A solution containing 24.7 gm of Ni (NO$_3$)$_2$.6H$_2$O and 2.278 gms. of NH$_4$ReO$_4$ in 67 mls. of water was prepared. 130 gms Girdler T869 support (⅛ inch extrusions) was prepared for impregnation by drying for 3 hours in a 120° C oven, and then allowed to cool in an evacuated flask. The Ni-Re solution was added to the dried, evacuated support through an addition funnel. After slurrying the support with the Ni-re solution, the impregnated support was dried at 120° C and then calcined for 3 hrs. at 300° C. Finally, the catalyst was activated by reduction in a stream of hydrogen for 3 hrs. at 300° C. After cooling to room temperature, the catalyst was stored under nitrogen prior to testing.

Preparation of 5% Ni-re on Girdler T1571 Support

A solution of 7.51 gms of Ni(NO$_3$)$_2$. 6H$_2$O and 0.6926 gm. of NH$_4$ReO$_4$ in 29 mls of water was prepared. The slurry was warmed to dissolve the salts. The support was prepared for ingregnation by drying for 3 hrs. at 120° C, and then cooled to room temperature under vacuum. The Ni-Re solution was added to the evacuated support via an addition funnel. The impregnated support was dried. Calcined and reduced as described previously for the preparation of Ni-re on T869 support.

B. Amination Reaction

Using the above prepared catalysts, a series of eight experiments outlined in the following table were conducted.

Table 5

| Exp. No. | Feed Mole Ratio NH$_3$/EG | Reaction Time (min.) | Catalyst Support | Initial Hydrogen Pressure | Wt. % H$_2$O in Product | Product Ratio EDA/DEDA |
|---|---|---|---|---|---|---|
| 1 | 15/1 | 45 | T869 | 200 | 10.0 | 5.7 |
| 2 | 25/1 | 45 | T869 | 300 | 8.7 | 10.6 |
| 3 | 15/1 | 90 | T869 | 300 | 11.7 | 5.3 |
| 4 | 25/1 | 90 | T869 | 200 | 8.6 | 12 |
| 5 | 15/1 | 45 | T1571 | 300 | 3.3 | Only MEA |
| 6 | 25/1 | 45 | T1571 | 200 | 2.5 | Only MEA |
| 7 | 15/1 | 90 | T1571 | 200 | 7.6 | 7.5 |
| 8 | 25/1 | 90 | T1571 | 300 | 5.8 | 12 |

All of the experiments outlined in the above table were conducted in a 0.5 l Parr autoclave constructed of stainless steel. In each experiment 5 grams of the specified catalyst and 18.6 grams of ethylene glycol were charged to the autoclave. Next the autoclave was pressurized with hydrogen to the specified initial pressure (PSIG), and then the required amount of ammonia was forced into the autoclave under nitrogen pressure. The amount of ammonia charged was either 76 gm or 128 gms depending upon the desired NH$_3$/EG feed mole ratio; 76 grams was charged for experiments 1, 3, 5, 7 and 128 grams was charged for experiments 2, 4, 6, 8.

After charging the ammonia the autoclave was heated, while being rocked, to 200° C. Upon reaching 200° C, the reaction temperature was maintained for the specified time, and then the autoclave heater was turned off. The autoclave was allowed to cool to room temperature, and the excess ammonia was slowly vented to reduce the pressure in the autoclave to atmospheric pressure.

In Table 5 above, for each experiment, the wt. % water in the final product (NH$_3$-free basis) is tabulated together with the area-ratio of EDA to DEDA obtained from gas-chromatographic analysis of the reaction mixtures. In all experiments the reaction mixtures were found to contain monoethanolamine and some unreacted ethyleneglycol. In experiments 1, 2, 3, 4, 7 and 8 the reaction mixture also contained ethylenediamine and piperazine.

The data reported in Table 5 confirms that T869 supported catalysts are more active than the T1571 catalysts and that degree of ethylene glycol conversion increases with increasing reaction time. Also shown is that the selectivity to ethylenediamine decreases as the conversion of ethylene glycol increases.

The data demonstrates the effect of varying the feed mole ratio of ammonia to ethylene glycol. Increasing the $NH_3$/EG feed mole ratio from 15/1 to 25/1 decreased the degree of ethylene glycol conversion. However, the increase in the $NH_3$/EG mole ratio increased the selectivity of the reaction to form ethylenediamine as compared with the piperazine product.

The conversion of ethylene glycol does not appear to be effected by the hydrogen pressure within the ranges examined in these experiments.

EXAMPLE 6

Ni-Re-B Catalyst

This example illustrates that a beneficial effect on activity can be obtained by adding Boron to a nickel-rhenium catalyst. This is accomplished by adding boric acid to the $Ni(NO_3)_2 \cdot 6H_2O$ and $NH_4ReO_4$ aqueous solution used to impregnate Girdler T869 support as described more fully below.

A solution containing 5.13 gm $Ni(NO_3)_2 \cdot 6H_2O$, 0.47 gms $NH_4ReO_4$ and 1.3 gm $H_3BO_3$ in 19 ml of distilled water was prepared. 18 gms of predried Girdler T869 support was placed in a 250 ml round bottom flask, and the flask was equipped with a vacuum adapter. The flask was evacuated by means of a vacuum pump, and then 9.5 mls of the above aqueous solution containing Ni-Re and $H_3BO_3$ was added to the support via a syringe. The impregnated support was re-dried at 120° C for 3 hours and impregnated as described above with a second 9.5 mls of the Ni/Re/B solution. The completely impregnated support was dried at 120° C for 3 hours, calcined at 300° C in a muffle furnace for 3 hours, and finally reduced at 300° C for 3 hours in a stream of hydrogen.

The above catalyst was tested for activity to convert ethylene-glycol to ethylene diamine, monoethanolamine and piperazine using the 0.5 1 Parr autoclave described above. The experiments conducted are outlined in Table 6 below. For comparison purposes, a similar catalyst prepared on T869 support except that it contained only nickel and rhenium was tested under the identical experimental conditions. In both experiments the reaction temperature was 200° C and the initial hydrogen pressure was 200 PSIG. The data in Table 6 shows that nickel-rhenium-boron containing catalyst is more active than the nickel-rhenium catalyst.

TABLE 6

| Exp. No. | Catalyst | Gms Catalyst | Gms $NH_3$ | Gms EG | Rxn Time | Wt. % $H_2O$ in Prod. | Product Ratio EDA DEDA |
|---|---|---|---|---|---|---|---|
| 1 | Ni—Re—B on T869 | 5 | 76 | 19 | 1 hr | 15.7 | 5.5 |
| 2 | Ni—Re on T869 | 5 | 76 | 19 | 1 hr | 9.5 | 6.8 |

EXAMPLE 7

Amination of Ethanol, 2-Propanol, and Acetone

A nickel-rhenium catalyst, further containing boron, was prepared to test its effectiveness in aminating ethanol, 2-propanol, and acetone.

A nickel-rhenium catalyst was prepared by impregnating 200 gms Girdlers's K306 support with 100 mls of an aqueous solution containing 64.5 gms of $Ni(NO_3)_2 \cdot 6$-$H_2O$, 5.95 gms of $NH_4ReO_4$, and 1.37 gm of $H_3BO_3$. The impregnated support was dried in an oven at 125° C for 3 hrs., calcined at 300° C for 3 hrs., and finally reduced in a stream of hydrogen for 3 hrs. at 300° C. The activated catalyst was stored under nitrogen until used.

All aminations were conducted in an 0.5l. rocker autoclave constructed of stainless steel. Five grams of the Ni-Re catalyst on K306 was placed in a rocker bomb autoclave which had been flushed out with nitrogen. The alcohol or ketone was placed in a test tube attached to a dip tube which fitted into the bomb autoclave. The bomb was sealed and pressurized to 200 psig with hydrogen. Next, the bomb was placed in the heating jacket of the rocking device, and the desired amount of liquid ammonia was pressured into the bomb via nitrogen pressurized Hoke cylinder. The $NH_3$-catalyst-$H_2$ mix was then heated to 190° C., and the rocker was switched on. On the first down-stroke the bomb was tipped sufficiently to permit the alcohol or ketone to dump from the test-tube, and come into contact with the catalyst 3-$H_2$ mixture. The reaction timer was started at this point. The particular reaction conditions for each of the three aminations are summarized in the following table:

| Run No. | Amination of (compound) | Gms. Catalyst | Gms. $NH_3$ | Gms. Compound | ° C. Rxn. Temp. | Rxn. Time |
|---|---|---|---|---|---|---|
| 1 | Ethanol | 5 | 79 | 21.3 | 190 | 2 hr. |
| 2 | 2-Propanol | 5 | 39.5 | 27.8 | 190 | 2 hr. |
| 3 | Acetone | 5 | 79 | 27 | 190 | 2 hr. |

After the desired reaction time, the liquid contents of the bomb were vented into a cold trap. After warming to room temperature, samples of the reaction products were analyzed by gas chromatography to determine the products of the reaction. The results obtained are tabulated below.

| Products | Run 1 Ethanol | Run 2 2-Propanol | Run 3 Acetone |
|---|---|---|---|
| Ammonia | 4.0 | 5.2 | 1.4 |
| Water | 13.07 | 15.67 | 37.4 |
| Ethylamine | 13.82 | — | — |
| Diethylamine | 0.21 | — | — |
| Triethylamine | 0.30 | — | — |
| Ethanol | 68.5 | — | — |
| Acetone | — | 0.11 | 16.95 |
| 2-Propanol | — | 51.31 | 12.06 |
| Isopropylamine | — | 27.42 | 28.14 |
| Diisopropylamine | — | 0.34 | 2.36 |

The high selectivity to the aminated products ethylamine and isopropylamine, are clear from the data. It is noted that in the case of acetone there is a substantial amount of the intermediate 2-propanol present in the reaction mixture but this is an expected intermediate in the ultimate production of the isopropylamine.

EXAMPLE 8

1,3-Propanediol Conversion

The nickel-rhenium based catalyst are also active catalysts for the conversion of higher molecular weight diols such as 1,3-propane-diol to diamines. This experiment shows that 1,3-propanediol is converted to a mixture of 1,3-propanediamine and 3-hydroxypropylamine over a nickel-rhenium catalyst.

A nickel-rhenium catalyst was prepared by impregnating 130 grams of Girdler support T869 with 67 mls of an aqueous solution containing 24.7 gm of Ni(NO$_3$)$_2$.6H$_2$O and 2.28 gms of NH$_4$ReO$_4$. The impregnated catalyst support was dried at 120° C for several hours, calcined at 300° C for 3 hours, and reduced in a stream of hydrogen at 300° C for 3 hours.

Five grams of the above catalyst was charged to a 0.5 l rocker autoclave, together with 32 gm of 1,3-propanediol. The autoclave was sealed, and pressurized to 200 PSIG with hydrogen. Next, 107 gm of anhydrous ammonia was pressured into the autoclave. The autoclave was heated to 200° C and maintained at 200° C for 2 hours. After cooling to room temperature the excess ammonia was vented from the autoclave, the autoclave was opened and the reaction mixture was collected.

Analysis of the reaction mixture by gas chromatography showed that significant amounts of 1,3-propanediamine and 3-hydroxypropylamine were produced during the reaction. Analysis of the crude reaction mixture for water content by Karl Fisher titration showed that the reaction mixture contained 15.2 wt.% water. This amount of water indicates that about 45% of the 1,3-propanediol charged had been converted to products.

EXAMPLE 9

Preparation and Testing of Catalysts Containing Ni, Re, Co, B on Girdler T869 Support Active catalysts containing nickel, rhenium, cobalt and boron have been prepared. The presence of boron in these catalysts has been shown not to be essential to the activity or selectivity although boron may play a role in the life of these catalysts.

Three catalysts have been prepared from a solution containing Ni(NO$_3$)$_2$.6H$_2$O, Co(NO$_3$)$_2$.6H$_2$O, NH$_4$ReO$_4$ and H$_3$BO$_3$ in distilled water which was used to impregnate a T869 catalyst support. The amounts of the metal salts used and the reduction temperature and time in the preparation of each catalyst is shown in Table 7 below. Each catalyst was calcined at 300° C for 3 hours prior to reduction.

The aforementioned three catalysts were tested for activity to aminate either ethyleneglycol or a mixture of monoethanolamine, diethanolamine, and triethanolamine. The amination experiments were conducted in a 0.5 liter rocker autoclave. The reagents, conditions and results are outlined in Table 8 below:

EXAMPLE 10

Preparation and Testing of Ni-Re Catalysts on Silica-Titania Supports

Three supports were prepared having SiO$_2$/TiO$_2$ mole ratios of 1/9, 1/1 and 9/1, respectively. Appropriate amounts of TiCl$_4$ and Si(OCH$_2$CH$_3$)$_4$ were mixed together in an addition funnel, and added dropwise to a rapidly stirring flask containing 550 grams of 28% NH$_3$-water solution (4.4 moles NH$_4$OH). After the addition was complete, the slurry was heated to 90° C, and stirring was continued for 1 hour. The slurry of SiO$_2$-TiO$_2$ was cooled to room temperature and filtered. The SiO$_2$-TiO$_2$ was washed with portions of distilled water until the washings gave a negative test for chloride ion with silver nitrate. The SiO$_2$-TiO$_2$ was air dried, then dried in an oven at 100° C for 20 hours and finally calcined at 500° C for 3 hours. The surface area of the powdered product was determined. The specific data for preparation of each of the three supports is indicated in the table below:

| SiO$_2$/TiO$_2$ | TiCl$_4$ gms. | Si(OC$_2$H$_5$)$_4$ gms | 28% NH$_2$-Water gms | Surface Area m$^2$/gm |
|---|---|---|---|---|
| 1/9 | 75.9 | 9.25 | 550 | 75 |
| 1/1 | 47.4 | 52.1 | 550 | 113 |
| 9/1 | 9.48 | 93.75 | 550 | 84 |

Three catalysts were prepared having the same 10% b.w. total Ni-Re content on each of the three SiO$_2$/TiO$_2$ supports described above. An impregnating solution containing 7.521 gms of Ni(NO$_3$)$_2$. 6H$_2$O and 0.693 gms of NH$_4$ReO$_4$ in 21 mls of water was prepared and used to impregnate 18 grams of each SiO$_2$/TiO$_2$ support. Each catalyst was thereafter calcined at a temperature of 300° C for 3 hours and thereafter reduced under hydrogen at a temperature of 300° C for 3 hours.

These catalysts were tested for activity to convert either ethyleneglycol or monoethanolamine to ethylenediamine. Each test was conducted by charging 5 grams of the respective catalyst together with an appropriate amount of NH$_3$, alcohol, and hydrogen to an 0.5 l rocker bomb autoclave. The reactants were heated to the desired reaction temperature. After a desired period Table 7

| Exp. No. | Ni(NO$_3$)$_2$.6H$_2$O grams | NH$_4$ReO$_4$ grams | Co(NO$_3$)$_2$. 6H$_2$O grams | H$_3$BO$_3$ grams | H$_2$O mls. | Reduction Temp ° C | Time |
|---|---|---|---|---|---|---|---|
| 1 | 3.062 | 0.282 | 0.919 |  | 18* | 300 | 3 hrs. |
| 2 | 2.64 | 0.487 | 5.288 | 0.337 | 18 | 300 | 3 hrs. |
| 3 | 2.749 | 0.3512 | 2.115 | 0.072 | 18 | 400 | 177 min. |

*Two impregnations were required, each using 9 mls of the metal solution, where the support was dried at 125° C between each impregnation.

of time, the contents of the bomb were analyzed for composition via a combination of gas chromatography, and Karl Fisher titration. Specific details of the tests are tabulated in the following Table 8.

In runs 1–3 significant amounts of MEA were present in the reaction mixture.

Table 8

| Exp. No. | Alcohol, grams | NH$_3$ grams | H$_2$ psig | Rxn Temp ° C | Rxn Time | Wt % H$_2$O in prod. | Product Ratio EDA/DEDA |
|---|---|---|---|---|---|---|---|
| 1 | EG, 19 | 76 | 200 | 200 | 2 hrs. | 11.05 | 4.94 |
| 2 | EG, 19 | 76 | 200 | 200 | 2 hrs. | 13.12 | 4.75 |
| 3 | MDT*, 19 | 106 | 200 | 185 | 1 hr. | 7.12 | 17.01 |

*Mixture: 90% wt. MEA; 7% wt. DEA; 3% wt., TEA

Table 9

| Exp. No. | Support SiO$_2$/TiO$_2$ | Alcohol | Grams Alcohol | Grams NH$_3$ | psig H$_2$ | Temp °C | Rsn Time (hours) | Wt.% H$_2$O in Prod. | Product Ratio EDA/DEDA |
|---|---|---|---|---|---|---|---|---|---|
| 1 | 9/1 | EG | 19 | 76 | 200 | 200 | 2 | 14.4 | 2.87 |
| 2 | 1/1 | EG | 19 | 76 | 200 | 200 | 2 | 19.2 | 3.65 |
| 3 | 1/9 | EG | 19 | 76 | 200 | 200 | 2 | 22.5 | 2.92 |
| 4 | 1/9 | MEA | 19 | 76 | 200 | 185 | .75 | 17.99 | 3.12 |
| 5 | 9/1 | MDT* | 19 | 106 | 200 | 185 | .5 | 10.5 | 8.68 |

*MDT = 90 wt% MEA, 7 wt% diethanolamine, and 3 wt% triethanolamine.

EXAMPLE 11

Preparation of an Active Ni-Re Catalyst Without Calcining

An aqueous solution containing 3.46 gm Ni(NO$_3$)$_2$.6-H$_2$O, 0.199 gm NH$_4$ReO$_4$, and 1.129 gm H$_3$BO$_3$ dissolved in 19 mls of distilled water was prepared. The above solution was used to impregnate 18 grams of Girdler T869 support. The impregnation was conducted in two steps, 9 mls of the above solution was used to impregnate 18 grams of the support. After drying at 125° C, the support was reimpregnated with the remaining 9 mls of solution. The fully impregnated support was dried at 125° C, and then reduced for 3 hours in a stream of hydrogen at 300° C followed by an additional 1 hour at 350° C. The reduced catalyst was grey in color and was stored under nitrogen until tested for activity.

The above prepared catalyst was tested under two sets of conditions.

Test 1

A 0.5 liter stainless steel rocker autoclave bomb was charged with 5 grams of the above catalyst (15-DCB-133) and 19 grams of a mixture of monoethanolamine, diethanolamine, and triethanolamine (90 wt% MEA, 7 wt% DEA, and 3 wt% TEA). The bomb was sealed and then pressurized to 200 psig with hydrogen and 106 grams of liquid ammonia was then added into the autoclave via a hoke cylinder.

The bomb was heated to 185° C and rocked for 45 minutes.

Test 2

The apparatus and procedure used for Test 2 was the same as that for Test 1 except the reaction temperature was 200° C, and the reaction time was 1 hour. After the reaction period for each test, a sample of the product was removed from the bomb and analyzed by gas chromatography. The compositions of the samples for Tests 1 and 2 are tabulated in the table below.

| Component | Test 1 Area % | Test 2 Area % |
|---|---|---|
| Water | 7.2 | 15.25 |
| EDA | 9.0 | 23.2 |
| DEDA | 0.29 | 2.7 |
| MEA | 73.1 | 56.2 |
| Heavies | 10.9 | 1.1 |

EXAMPLE 12

Variables in Catalyst Preparation

In order to determine if the activity of Ni/Re based catalysts is effected by changing either the Ni/Re atom ratio, the method of support impregnation, the calcining temperature, or the reduction temperature, a series of eight experiments have been conducted. A fifth variable also included in the experimental set was the support used; both Girdler T869 and Girdler T372 were examined. The experiments conducted are outlined in Table 10.

The catalysts were prepared as required for testing. For example, for experiment number 1 a catalyst was prepared by precipitating Ni and Re on Girdler T372 support. The metals were precipitated from an aqueous solution containing Ni(NO$_3$)$_2$.6H$_2$O, NH$_4$ReO$_4$ (2 to 1 mole ratio), and Girdler T372 by the addition of ammonium carbonate. After carbonate addition, the resulting slurry was evaporated to dryness to give the metal coated support. The dried support was placed in a muffle oven and calcined for 3 hours at 300° C, and finally the catalyst was activated by reduction for 3 hours at 300° C in a stream of hydrogen.

The preparation of the catalysts without a precipitant were conducted as described above except that the addition of ammonium carbonate to the metal-support slurry was omitted.

For each experiment 5 gms catalyst (5% total metal on support listed on the table), 26 gms MEA, 72 gms ammonia, and 200 psig hydrogen gas were charged to a 500 ml rocker autoclave. The reaction time was 6 hours and reaction temperature was 225° C.

The data obtained for the 8 runs are tabulated in Table 10. The water analysis was by Karl Fisher titration. Two values for the % water are shown for runs 3, 5, and 7 as these experiments were repeated by using new batches of the catalysts prepared as described earlier.

Table 10

| Exp. No. | Ratio Ni/Re | Precipitant Used | Calcining Temp °C | Reduction Temp °C | Support Used | % Water |
|---|---|---|---|---|---|---|
| 1 | 2/1 | (NH$_4$)$_2$CO$_3$ | 300 | 300 | T372 | 8.7, 11.6, 9.0 |
| 2 | 20/1 | (NH$_4$)$_2$CO$_3$ | 300 | 600 | T372 | 26.8 |
| 3 | 2/1 | None | 300 | 600 | T869 | 9.09*, 24.8 |
| 4 | 20/1 | None | 300 | 300 | T869 | 33.15 |
| 5 | 2/1 | (NH$_4$)$_2$CO$_3$ | 500 | 600 | T869 | 28.9, 30.98 |
| 6 | 20/1 | (NH$_4$)$_2$CO$_3$ | 500 | 300 | T869 | 30.2 |
| 7 | 2/1 | None | 500 | 300 | T372 | 8.0, 8.69 |

Table 10-continued

| Exp. No. | Ratio Ni/Re | Precipitant Used | Calcining Temp °C | Reduction Temp °C | Support Used | % Water[a,b] |
|---|---|---|---|---|---|---|
| 8 | 20/1 | None | 500 | 600 | T372 | 29.3 |

*The value 9.09 is considered a blunder, the correct value being 24.88. A statistical analysis of all the results and the value 24.88 from the second repeated run confirm this.

What is claimed is:

1. In the process for aminating a lower aliphatic alkane derivative with ammonia in the presence of a solid catalyst wherein the products comprise both economically desirable alkylamines and undesirable by-products of lesser economic significance, the improvement in selectivity and increased conversion, evidenced by the production of a substantially greater amount of said valuable alkylamines together with concomitant reduction in the yield of undesirable by-products from a given alkane charge, which comprises reacting under amination conditions said alkane charge with ammonia in the presence of hydrogen and a nickel-rhenium catalyst comprising rhenium and nickel impregnated on a support material selected from the group consisting of aluminas, silicas, silica-aluminas, kieselguhrs or diatomaceous earths and silica-titanias, wherein said catalyst has a total nickel and rhenium metal content of 3–30% by weight of the support and the atom ratio of the nickel to the rehnium present is in the range from about 2:1 to about 30:1.

2. The process of claim 1 wherein said alkane derivative contains from one to six carbon atoms and at least one functional group capable of being replaced by an amino group by the catalytic amination process.

3. The process of claim 1 wherein said alkane derivative contains from one to six carbon atoms and at least one hydroxy functional group.

4. The process of claim 1 wherein the desirable alkylamine product is ethylenediamine and the alkane derivative is selected from the group consisting of ethylene glycol, monoethanolamine, and mixtures thereof.

5. The process of claim 1 wherein said catalyst is comprised of boron in addition to nickel and rhenium.

6. The process of claim 1 wherein said catalyst is comprised of boron and cobalt in addition to nickel and rhenium.

7. The process of claim 1 wherein said support material is an α-alumina.

8. The process of claim 1 wherein said support material is a silica-alumina.

9. The process of claim 4 wherein the ammonia is present in an amount greater than the stochiometric amount required by the alkane derivative coreactant that is present.

10. The process of claim 9 wherein the ammonia is present in an amount in the range 2–15 times the stochiometric amount required by the alkane derivative coreactant.

11. A process for producing lower aminoalkanes by the catalytic amination of lower aliphatic alkane derivatives selected from lower alkanemono-ols, lower alkanediols, lower alkanolamines, and mixtures thereof, said process comprising the step of reacting said alkane derivatives with ammonia under pressure, at a temperature of from 125° C to 350° C, and in the presence of hydrogen and an active nickel-rhenium catalyst, said catalyst comprising rhenium and nickel impregnated on a support material selected from the group consisting of aluminas, silicas, silica-aluminas, kieselguhrs or diatomaceous earths, and silicatitanias, wherein the nickel and rhenium metal content is from 3–30% by weight of the support material and the atom ratio of the nickel to the rhenium present is in the range from about 2:1 to about 30:1, and wherein said catalyst is present in a catalytic amount.

12. The process of claim 11 wherein the catalyst is activated by heating it in the presence of hydrogen in the temperature range 200°–600° C.

13. The process of claim 11 wherein the pressure during the reaction is in the range of 500 to 5,000 psig.

14. The process of claim 11 wherein the lower aliphatic alcohol is 1,3-propanediol.

15. The process of claim 11 wherein the lower aliphatic alcohol is selected from ethanol and 2-propanol.

16. A process for producing ethylenediamine by the catalytic amination of a compound selected from the group consisting of ethylene glycol, monoethanolamine, ethyleneoxide, ethyleneimine, and mixtures thereof, said process comprising reacting said compound with ammonia in the presence of hydrogen and a Ni-Re catalyst comprising rhenium and nickel impregnated on a support material selected from the group consisting of aluminas, silicas, silica-aluminas, kieselguhrs or diatomaceous earths, and silica-titanias, said catalyst having a total nickel and rhenium metal content of 3–30% by weight of the support and a nickel to rhenium atom ratio in the range from about 2:1 to about 30:1 and wherein said catalyst is activated in the presence of hydrogen at elevated temperature, and wherein the temperature of the amination reaction is in the range 125°–350° C, the pressure is 500–5000 psig and the amount of ammonia present is in excess of 2 times the stochiometric amount required by the compound.

* * * * *

UNITED STATES PATENT OFFICE
CERTIFICATE OF CORRECTION

Patent No. 4,123,462  Dated October 31, 1978

Inventor(s) D.C. Best

It is certified that error appears in the above-identified patent and that said Letters Patent are hereby corrected as shown below:

Column 5, line 56 "sown" should read "shown".

Column 20, line 21 "3-$H_2$" should read "$NH_3$-$H_2$".

Signed and Sealed this

Thirteenth Day of March 1979

[SEAL]

Attest:

RUTH C. MASON
Attesting Officer

DONALD W. BANNER
Commissioner of Patents and Trademarks